(12) United States Patent
Hu et al.

(10) Patent No.: US 8,609,862 B2
(45) Date of Patent: Dec. 17, 2013

(54) USE OF AN ADRENAL HORMONE-MODIFYING AGENT

(75) Inventors: Qi-Ying Hu, Needham, MA (US); Gary Michael Ksander, Amherst, NH (US); Erik Meredith, Hudson, MA (US); Lauren G. Monovich, Belmont, MA (US); Julien Papillon, Somerville, MA (US); Christoph Schumacher, Bettingen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/521,548

(22) PCT Filed: Jan. 13, 2011

(86) PCT No.: PCT/US2011/021100
§ 371 (c)(1),
(2), (4) Date: Jul. 11, 2012

(87) PCT Pub. No.: WO2011/088188
PCT Pub. Date: Jul. 21, 2011

(65) Prior Publication Data
US 2012/0295888 A1    Nov. 22, 2012

Related U.S. Application Data

(60) Provisional application No. 61/294,980, filed on Jan. 14, 2010.

(51) Int. Cl.
*A61K 31/4188* (2006.01)
*C07D 235/02* (2006.01)

(52) U.S. Cl.
USPC ........................ 548/302.7; 514/393

(58) Field of Classification Search
USPC ........................................ 548/302.7
See application file for complete search history.

(56) References Cited

U.S. PATENT DOCUMENTS

| | | | |
|---|---|---|---|
| 4,889,861 A * | 12/1989 | Browne ................ | 514/300 |
| 2006/0074058 A1 * | 4/2006 | Holmes et al. ............. | 514/171 |
| 2007/0049616 A1 * | 3/2007 | Ksander et al. ............. | 514/303 |
| 2012/0277215 A1 * | 11/2012 | Ksander et al. .......... | 514/214.02 |

FOREIGN PATENT DOCUMENTS

| | | |
|---|---|---|
| EP | 1 886 695 A1 | 2/2008 |
| EP | 2095819 A1 | 9/2009 |
| WO | 89/07442 A1 | 8/1989 |
| WO | 96/11684 A1 | 4/1996 |
| WO | 2007/024945 A1 | 3/2007 |
| WO | 2007/139992 A2 | 12/2007 |

OTHER PUBLICATIONS

Argilés et al., Journal of Cachexia Sarcopenia Muscle (May 8, 2012), 3, pp. 73-76.*
Juszczak et al., Endokrynologia Polska, 64(2), (2013), pp. 166-174.*
Ulla Enberg et al: "New aspects on primary aldosteronism", Neurochemical Research, Kluwer Academic Publishers-Plenum Publishers, NE, vol. 28, No. 2, Feb. 1, 2003, pp. 327-332.

* cited by examiner

*Primary Examiner* — Laura L. Stockton
(74) *Attorney, Agent, or Firm* — Cozette M McAvoy

(57) ABSTRACT

The present invention relates to a method of treating a disease or disorder characterised by increased stress hormone levels and/or decreased androgen hormone levels in a subject, comprising administering to the subject a therapeutically effective amount of a compound represented by formula (I):

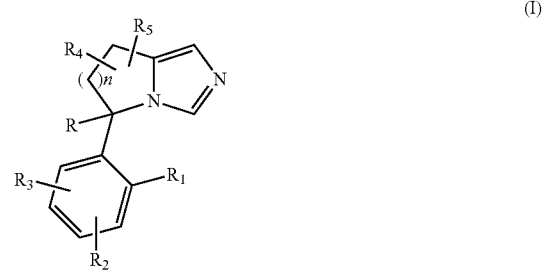

(I)

wherein n is 1 or 3; R is hydrogen or —C(O)N($R_a$)($R_b$) wherein $R_a$ and $R_b$ are independently —($C_1$-$C_4$)alkyl, or —($C_1$-$C_4$)alkyl-($C_5$-$C_7$)aryl, wherein each of $R_a$ and $R_b$ is optionally substituted by —($C_1$-$C_4$)alkoxy; $R_1$, $R_2$, and $R_3$, are independently hydrogen, halogen, cyano or —($C_6$-$C_{10}$) aryl, wherein said —($C_6$-$C_{10}$)aryl is optionally substituted by halogen, with the proviso that no more than one of $R_1$, $R_2$, and $R_3$ is hydrogen; and $R_4$ and $R_5$ are hydrogen; or a pharmaceutically acceptable salt thereof.

5 Claims, 2 Drawing Sheets

USE OF AN ADRENAL HORMONE-MODIFYING AGENT

FIELD OF INVENTION

The invention relates to the use of a compound with adrenal hormone-modifying properties in disease states characterised by increased stress hormone levels and/or decreased androgen hormone levels.

BACKGROUND OF THE INVENTION

Steroidogenesis in the adrenal gland occurs via highly related and controlled cytochrom P450 enzymes. Inhibition of Aldosterone Synthase or the enzyme cytochrom P450 11B2 (CYP11B2) represents a new pharmacological strategy to reduce excessive aldosterone levels. Aldosterone is a mineralocorticoid that is mainly synthesized in the adrenal gland and released into the circulation to control in the renal epithelium the sodium/potassium balance and thus water homeostasis and blood pressure as well as the in non-epithelial tissue of heart and kidney the formation of extracellular matrix and organ remodeling. Aldosterone synthase mediates in the adrenal gland the terminal and rate-limiting conversion of 11-deoxycorticosterone to corticosterone via 11-beta-hydroxylation, the conversion of corticosterone to 18-hydroxycorticosterone via 18-methylhydroxylation and finally the conversion of 18-hydroxy-corticosterone to aldosterone via 18-methyloxidation. The activity and expression of the enzyme is mainly regulated by angiotensin II, potassium and adrenocorticotropin. These regulators of aldosterone synthase are sensitive to the actions of aldosterone and the physiological circadian rhythm and as such create an endocrine feedback loop. Angiotensin II is produced upon stimulation of renin activity that is triggered via sodium loss and blood pressure decrease due to hypoaldosteronemic states. Potassium is retained in exchange to sodium loss in hypoaldosteronemic conditions. Finally, adrenocorticotropin is produced from the pituitary gland in response to low glucocorticoid levels and the circadian rhythm. Hence, a selective inhibition of aldosterone synthase and a reduction of aldosterone secretion is counteracted with the stimulation of renin and the generation of angiotensin II as well as by a retention of potassium; both increased angiotensin II and potassium levels being potent stimulators of aldosterone synthase activity and thus aldosterone secretion. The circadian rhythm upon aldosterone synthase inhibition is blunted for aldosterone yet adrenocorticotropin levels are not significantly changed as glucocorticoids are the main regulators of adrenocorticotropin secretion. The rate-limiting enzyme of cortisol secretion is the adrenal enzyme 11-beta-hydroxylase or cytochrom P450 11B1 (CYP11B1) that converts 11-deoxycortisol to cortisol. Cortisol levels are controlled via the hypothalamic-pituitary-adrenal feedback loop by controlling the release of adrenocorticotropin (ACTH). Adrenocorticoptropin stimulates in the adrenal gland the early and late steroidogenic reactions leading to the synthesis of cortisol but also dehydroepiandrosterone and androstendione (see FIG. 1, a diagram for adrenal steroidogenesis). The cortisol-producing enzyme CYP11B1 shows a high sequence homology of 95% at the amino acid level to the aldosterone-producing enzyme CYP11B2. Therefore, a compound targeted at aldosterone synthase to reduce excessive aldosterone secretion needs to be tested for its enzyme selectivity.

SUMMARY OF THE INVENTION

In one aspect, the present invention provides a method of treating a disease or disorder characterised by increased stress hormone levels and/or decreased androgen hormone levels in a subject, comprising administering to the subject a therapeutically effective amount of a compound represented by formula (I) or a pharmaceutically acceptable salt thereof.

In another aspect, there is provided a method of treating heart failure, cachexia, acute coronary syndrome, chronic stress syndrome, cushing's syndrome or metabolic syndrome, comprising administering to the subject a therapeutically effective amount of a compound represented by formula (I) or a pharmaceutically acceptable salt thereof.

In a further aspect, there is provided the use of a compound of formula (I) or a pharmaceutically acceptable salt thereof, for the preparation of a pharmaceutical composition for the treatment of a disorder or disease characterised by increased stress hormone levels and/or decreased androgen hormone levels in a subject In a further aspect, there is provided the use of a compound of formula (I) or a pharmaceutically acceptable salt thereof, in the treatment of a disorder or disease characterised by increased stress hormone levels and/or decreased androgen hormone levels in a subject.

In another aspect, the present invention provides the use of a compound of formula (I) or a pharmaceutically acceptable salt thereof, for the preparation of a pharmaceutical composition for the treatment of a disorder or disease selected from heart failure, cachexia, acute coronary syndrome, chronic stress syndrome, cushing's syndrome or metabolic syndrome.

In a further aspect, there is provided the use of a compound of formula (I) or a pharmaceutically acceptable salt thereof, in the treatment of a disorder or disease selected from heart failure, cachexia, acute coronary syndrome, chronic stress syndrome, cushing's syndrome or metabolic syndrome.

DETAILED DESCRIPTION OF THE INVENTION

Figure 1:
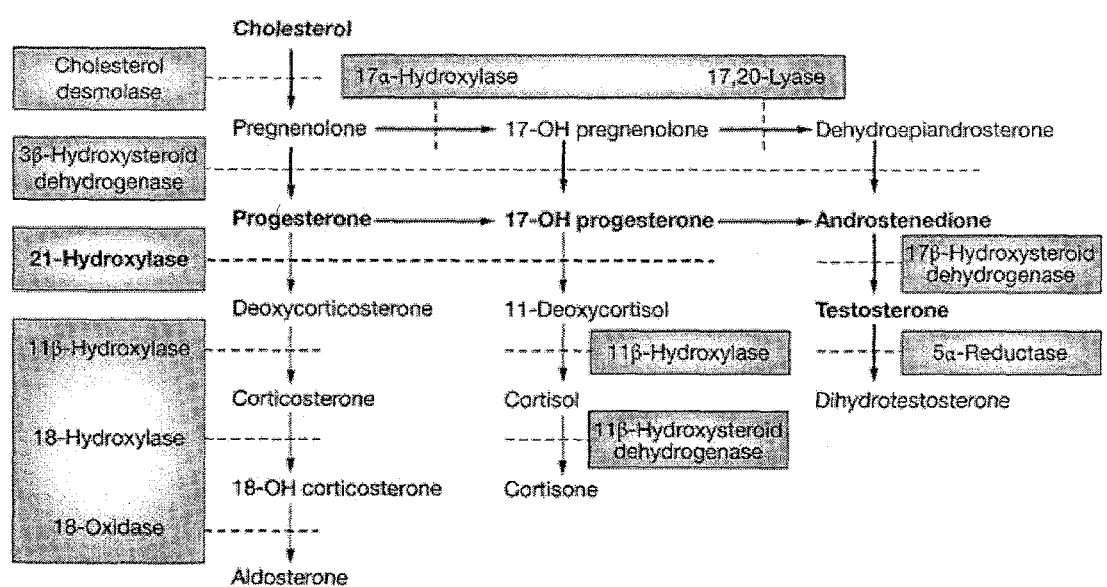
FIG. 1, a diagram for adrenal steroidogenesis.

The compounds that can be used in the present invention is described by using the following formula (I)

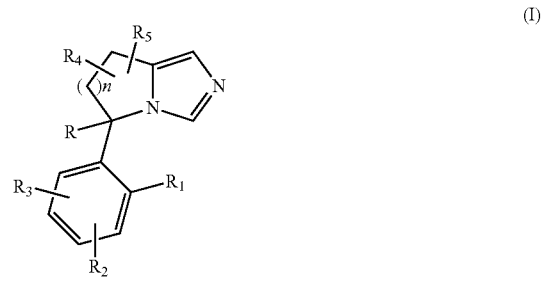

wherein n is 1 or 3;

R is hydrogen or —C(O)N($R_a$)($R_b$) wherein $R_a$ and $R_b$ are independently —($C_1$-$C_4$)alkyl, or —($C_1$-$C_4$)alkyl-($C_5$-$C_7$) aryl, wherein each of $R_a$ and $R_b$ is optionally substituted by —($C_1$-$C_4$) alkoxy;

$R_1$, $R_2$, and $R_3$, are independently hydrogen, halogen, cyano or —($C_6$-$C_{10}$)aryl, wherein said —($C_6$-$C_{10}$)aryl is optionally substituted by halogen, with the proviso that no more than one of $R_1$, $R_2$, and $R_3$ is hydrogen; and $R_4$ and $R_5$ are hydrogen; or a pharmaceutically acceptable salt thereof.

In one embodiment the compound of Formula (I) is 4-[(5R)-6,7-dihydro-5H-pyrrolo[1,2-c]imidazol-5-yl]-3-fluororbenzonitrile having formula (II).

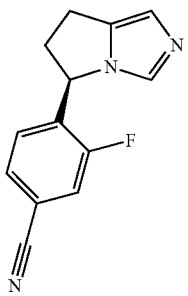 [SMILES: N#Cc1ccc([C@H]2CCc3cncn32)c(F)c1]

As used herein, the term "alkyl" refers to a fully saturated branched or unbranched hydrocarbon moiety. Preferably the alkyl comprises 1 to 6 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. As used herein, the term "lower alkoxy" refers to the alkoxy groups having about 1-7 preferably about 1-4 carbons.

The term "aryl" refers to monocyclic or bicyclic aromatic hydrocarbon groups having 6-20 carbon atoms in the ring portion. Preferably, the aryl is a $(C_6-C_{10})$aryl. Non-limiting examples include phenyl, biphenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, HS—, alkyl-S—, aryl-S—, nitro, cyano, carboxy, alkyl-O—C(O)—, carbamoyl, alkyl-S(O)—, sulfonyl, sulfonamido, heterocyclyl and the like, wherein R is independently hydrogen, alkyl, aryl, heteroaryl, aryl-alkyl-, heteroaryl-alkyl- and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "halogen" or "halo" refers to fluoro, chloro, bromo, and iodo.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

In another embodiment the compound of Formula (I) is 4-[(5R)-6,7-dihydro-5H-pyrrolo[1,2-c]imidazol-5-yl]-3-fluororbenzonitrile dihydrogenphosphate salt.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, *Remington's Pharmaceutical Sciences,* 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The term "therapeutically effective amount" of a compound of the present invention refers to an amount of the compound of the present invention that will elicit the biological or medical response of a subject, or ameliorate symptoms, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) characterised in excessive stress hormone levels and/or insufficient androgen hormone levels or (ii) associated with activities of excessive stress hormone levels and/or insufficient androgen hormone levels, or (iii) characterised by abnormal activities of excessive stress hormone levels and/or insufficient androgen hormone levels; or (2) reducing or inhibiting the activities of excessive stress hormone levels and/or reducing or inhibiting the activity of steroidogenic enzymes that indirectly lead to insufficient androgen hormone levels, or (3) reducing or inhibiting the synthesis of excessively produced stress hormone levels and/or increasing androgen hormone levels.

In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activities of excessive stress hormone levels and/or increasing androgen hormone levels; or at least partially reducing or inhibiting the synthesis of excessively produced stress hormone levels and/or increasing androgen hormone levels.

As used herein, the term "subject" refers to an animal. In one embodiment, the animal is a mammal. A subject also refers to for example, primates (e.g., humans), cows, sheep, goats, horses, dogs, cats, rabbits, rats, mice, fish, birds and the like. In one embodiment, the subject is a human.

As used throughout in this patent application, the levels of the hormones as measured in a subject could be in any sample taken from said subject. In one embodiment the levels are measured in a blood sample. In another embodiment the levels are determined from a plasma sample.

As used herein, the term "a disorder" or "a disease" refers to any derangement or abnormality of function; a morbid physical or mental state. See *Dorland's Illustrated Medical Dictionary*, (W.B. Saunders Co. 27th ed. 1988).

As used herein, the term "treating" or "treatment" of any disease or disorder refers in one embodiment, to partially or totally ameliorating the disease or disorder (i.e., arresting or reducing the development of the disease or at least one of the clinical symptoms thereof). In another embodiment "treating" or "treatment" refers to partially or totally ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Any asymmetric carbon atom on the compounds of the present invention can be present in the (R)-, (S)- or (R,S)-configuration, preferably in the (R)- or (S)-configuration. Substituents at atoms with unsaturated bonds may, if possible, be present in cis-(Z)- or trans (E)-form. Therefore, the compounds of the present invention can be in the form of one of the possible isomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, the imidazolyl moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O, O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

In addition, the present invention contemplates compounds of Formula (I) to include the free form, a salt form, or prodrug derivatives thereof. The compounds can be obtained in the form of hydrates or include solvents used for their crystallization.

The compounds of the present invention can be synthesized or produced and characterized by methods as described in WO2007/024945, the contents thereof is herein incorporated by reference.

In another embodiment, the methods include using the compounds according to Formula (I) to treat diseases or disorder described above, wherein the compounds, including isomers, optical isomers or pharmaceutically acceptable salts thereof, preferably including isomers, optical isomers, are selected from 4'-fluoro-6-(6,7,8,9-tetrahydro-5H-imidazo[1,5-a]azepin-5-yl)biphenyl-3-carbonitrile;

3-bromo-4-(6,7,8,9-tetrahydro-5H-imidazo[1,5-a]azepin-5-yl)benzonitrile;

5-(2-chloro-4-cyanophenyl)-N-(4-methoxybenzyl)-N-methyl-6,7-dihydro-5H-pyrrolo[1,2-c]imidazole-5-carboxamide;

5-(4-Cyano-2-methoxyphenyl)-6,7-dihydro-5H-pyrrolo[1,2-c]imidazole-5-carboxylic acid (4-fluorobenzyl)methylamide;

4-(6,7-Dihydro-5H-pyrrolo[1,2-c]imidazol-5-yl)-3-fluorobenzonitrile;

5-(3-fluoro-4-methoxyphenyl)-6,7-dihydro-5H-pyrrolo[1,2-c]imidazole;

5-(2-Chloro-4-cyanophenyl)-6,7-dihydro-5H-pyrrolo[1,2-c]imidazole-5-carboxylic acid 4-fluorobenzyl ester;

5-(2-Bromo-4-fluorophenyl)-6,7,8,9-tetrahydro-5H-imidazo[1,5-a]azepine;

2-Bromo-4-(6,7,8,9-tetrahydro-5H-imidazo[1,5-a]azepin-5-yl)benzonitrile;

3-Pyridin-3-yl-4-(6,7,8,9-tetrahydro-5H-imidazo[1,5-a]
azepin-5-yl)benzonitrile; and
3-Chloro-4-(6,7,8,9-tetrahydro-5H-imidazo[1,5-a]azepin-5-yl)benzonitrile;
in particular selected from
4'-fluoro-6-(6,7,8,9-tetrahydro-5H-imidazo[1,5-a]azepin-5-yl)biphenyl-3-carbonitrile;
3-bromo-4-(6,7,8,9-tetrahydro-5H-imidazo[1,5-a]azepin-5-yl)benzonitrile;
5-(2-chloro-4-cyanophenyl)-N-(4-methoxybenzyl)-N-methyl-6,7-dihydro-5H-pyrrolo[1,2-c]imidazole-5-carboxamide; and
4-(6,7-Dihydro-5H-pyrrolo[1,2-c]imidazol-5-yl)-3-fluorobenzonitrile.

Preferably a compound of formula (I), as described herein, is of the formula (4-[(5R)-6,7-dihydro-5H-pyrrolo[1,2-c]imidazol-5-yl]-3-fluororbenzonitrile or a pharmaceutically acceptable salt thereof, in particular (4-[(5R)-6,7-dihydro-5H-pyrrolo[1,2-c]imidazol-5-yl]-3-fluororbenzonitrile dihydrogen phosphate. A salt of a compound of formula (I), as defined herein, preferably a phosphate salt, such dihydrogen phosphate, may be prepared according to standard methods known to the person skilled in the art, for example as described in Chem. Commun., 2007, 419-421 (2007); in Development of a pharmaceutical cocrystal of a monophosphate salt with phosphoric acid Alex M. Chen, Martha E. Ellison, Andrey Peresypkin, Robert M. Wenslow, Narayan Variankaval, Cecile G. Savarin, Theresa K. Natishan, a David J. Mathre, a Peter G. Dormer, a Danielle H. Euler, b Richard G. Ball, Zhixiong Ye, Yaling Wanga and Ivan Santos; in Handbook of Pharmaceutical Salts: Properties, Selection, and Use Edited by P. Heinrich Stahl and Camile G. Wermuth. VHCA, Verlag Helvetica Chimica Acta, Zürich, Switzerland, and Wiley-VCH, Weinheim, Germany. 2002; in Organic Process Research & Development 2000, 4, 427-435 Salt Selection and Optimisation Procedures for Pharmaceutical New Chemical Entities Richard J. Bastin, Michael J. Bowker, and Bryan J. Slater; in Advanced Drug Delivery Reviews 56 (2004) 275-300, High-throughput crystallization: polymorphs, salts, co-crystals and solvates of pharmaceutical solids Sherry L. Morissettea,*, O"rn Almarssona, Matthew L. Petersona, Julius F. Remenara, Michael J. Reada, Anthony V. Lemmoa, Steve Ellisa, Michael J. Cimab, Colin R. Gardner; and in Journal of Pharmaceutical Sciences, VOL. 96, NO. 5, MAY 2007, Structure, Solubility, Screening, and Synthesis of Molecular Salts, Black, S, N., Collier, E. A., Davey, R. J. and Roberts, R. J.

According to the invention a compound of formula (I) and/or a pharmaceutically acceptable salt thereof represents a pleiotropic modifier of adrenal steroidogenesis when administered to a subject. A compound of formula (I) maintains or lowers cortisol levels when administered to a subject. A compound of formula (I) increases 11-deoxycortisol levels when administered to a subject. A compound of formula (I) increases levels of adreonocorticotropin when administered to a subject. A compound of formula (I) increases levels of 11-deoxycorticosterone. A compound of formula (I) increases adrenal androgens when administered to a subject.

In example 1, it has been shown that a compound of formula (I) namely (4-[(5R)-6,7-dihydro-5H-pyrrolo[1,2-c]imidazol-5-yl]-3-fluororbenzonitrile dihydrogen phosphate represents a pleiotropic modifier of adrenal steroidogenesis when administered to subject. It is shown in FIG. 1, that 4-[(5R)-6,7-dihydro-5H-pyrrolo[1,2-c]imidazol-5-yl]-3-fluororbenzonitrile dihydrogen phosphate maintains or lowers cortisol levels when administered to a subject. It is further shown that 4-[(5R)-6,7-dihydro-5H-pyrrolo[1,2-c]imidazol-5-yl]-3-fluororbenzonitrile dihydrogen phosphate increases 11-deoxycortisol levels when administered to a subject. 4-[(5R)-6,7-dihydro-5H-pyrrolo[1,2-c]imidazol-5-yl]-3-fluororbenzonitrile dihydrogen phosphate increases levels of adreonocorticotropin when administered to a subject. 4-[(5R)-6,7-dihydro-5H-pyrrolo[1,2-c]imidazol-5-yl]-3-fluororbenzonitrile dihydrogen phosphate increases levels of 11-deoxycorticosterone. 4-[(5R)-6,7-dihydro-5H-pyrrolo[1,2-c]imidazol-5-yl]-3-fluororbenzonitrile dihydrogen phosphate increases adrenal androgens when administered to a subject.

The clinical relevance of increased stress hormone levels and/or decreased androgen hormone levels has been shown for the following conditions.
(i) chronic heart failure
(ii) chronic heart failure with impaired exercise tolerance
(iii) chronic heart failure with muscle weakness
(iv) cardiac cachexia
(v) COPD-induced cachexia
(vi) cirrhosis-induced cachexia
(vii) tumor-induced cachexia
(viii) viral (HIV)-induced cachexia
(ix) acute heart failure
(x) acute decompensated heart failure
(xi) acute coronary syndrome
(xii) chronic stress syndrome
(xiii) Cushing's syndrome
(xiv) metabolic syndrome
(xv) hypercortisolemia (i) Chronic heart failure as well as chronic heart failure conditions with impaired exercise tolerance (ii) and muscle weakness (iv) show raised plasma aldosterone levels as shown by Bolger et al. Circulation 2002; 106:92-99, a raised plasma to dihydroepiandrosterone ratio as shown by Anker et al. European Heart Journal 1999; 20:683-693 and decreased androgen levels as shown by Jankowaska et al., Circulation 2006; 114:1829-1837.

(iv) Cardiac cachexia is a serious complication of chronic heart failure as patients suffer from a general loss of fat tissue, lean tissue and bone tissue. Cardiac cachexia patients show raised plasma levels of aldosterone and cortisol as well as reduced levels of dehydroepiandrosterone as described by Anker et al., Circulation 1997; 96:526-534 and illustrated in WO 2000/21509 and US 2009/0023639.

(v) COPD-induced cachexia, cirrhosis-induced cachexia (vi), tumor-induced cachexia (vii) and viral (HIV)-induced cachexia (viii) are characterized by increased plasma aldosterone levels as documented in WO 2000/21509 or US 2009/0023639 and have been treated with anabolic androgen or androgen-derivatives as reported by Yeh et al., Chest 2002; 122:421-428 and by Cuerda et al., Nutrition Clinical Practice 2005 20; 93-97.

(ix-x) Plasma cortisol predict cardiac events such as death and hospitalization in patients with heart failure according to Yamaji et al. Circulation Heart Failure 2009; 2:608-613.

(xi) Myocardial infarction raises cortisol levels that affect cardiac remodeling as indicated by Mihailidu et al., Hypertension 2009 in press. The magnitude of the cortisol response is related to the size of the ensuing infarction as shown by Bain et al., International Journal of Cardiology 1992; 27:145-150.

(xii) Chronic stress disorders with its physical and psychological ramifications has been associated with excessive aldosterone and cortisol levels according to Kubzansky and Adler, Neuroscience and Biobehavioral Reviews, 2009; 5:1-

7. Particularly, excessive and persistent cortisol secretion can lead to depression, hyperglycemia and the suppression of the immune system.

(xiii) Cushing's syndrome describes a condition of chronically excessive cortisol release. The cortisol excess may orginate directly from an adrenocortical tumor or secondarily from a pituitary (Cushing's Disease) or ectopic tumor that releases adrenocorticotropin as illustrated by Boscaro and Arnaldi, Journal of Clinical Endocrinology and Metabolism 2009; 94:3121-3131.

(xiv) Metabolic syndrome defines a state of metabolic dysregulation characterized by insulin resistance and a predisposition to type 2 diabetes, central and visceral obesity, hypertension and dyslipidemia. The metabolic dysregulation can be caused by an underlying endocrine imbalance mediated by the adrenal steroids aldosterone and cortisol as reported by Kidamby et al. Hypertension 2007; 49:704-711.

(xv) Hypercortisolemia refers to conditions that are characterized by high levels of circulating cortisol. High levels of plasma cortisol may directly contribute to a pathological condition, represent a sign of a pathological condition or be of non-pathological nature.

The invention relates to the use of a compound of formula (I) and/or a pharmaceutically acceptable salt thereof or any other form of it as as discussed above with adrenal hormone-modifying properties as treatment for conditions that are characterized by excessive stress hormone levels and or insufficient androgen hormone levels such as heart failure, cachexia, acute coronary syndrome, chronic stress syndrome, hypercortisolemia, cushing's syndrome or metabolic syndrome, in particular heart failure, cachexia, acute coronary syndrome, chronic stress syndrome, cushing's syndrome or metabolic syndrome. Heart failure could be both acute heart failure and chronic heart failure. Acute heart failure could be acute decompensated heart failure. Chronic heart failure could be associated with impaired exercise tolerance and or with muscle weakness. Cachexia could be cardiac cachexia, COPD-induced cachexia, cirrhosis-induced cachexia tumor-induced cachexia or viral (HIV)-induced cachexia. Chronic stress syndrome may include depression, hyperglycemia and immunesuppression. Cushing's syndrome can include hypercortisolism due to adrenocortical, pituitary or ectopic tumors. Metabolic syndrome could include obesity, diabetes, hypertension, dyslipidemia and atherosclerosis. The compounds of Formula (I) have adrenal hormone-modifying properties in diseases or conditions characterised by increased stress hormone levels and/or decreased androgen hormone levels as shown in the experimental section.

The present invention provides a method of lowering or maintaining cortisol levels in a subject by administering a therapeutically efficient dose of a compound of formula (I).

The present invention provides a method of treating a disorder, disease or condition characterised by decreased or insufficient androgen hormone levels in a subject by administering a therapeutically efficient dose of a compound of formula (I).

The present invention provides a compound of formula (I), or pharmaceutically acceptable salt thereof, for use in the treatment of a disorder, disease or condition characterised by decreased or insufficient androgen hormone levels.

The present invention provides a method of treating a disorder, disease or condition characterised by excessive stress hormone levels, such as aldosterone and cortisol levels in a subject by administering a therapeutically efficient dose of a compound of formula (I).

The present invention provides a compound of formula (I), or pharmaceutically acceptable salt thereof, for use in the treatment of a disorder, disease or condition characterised by excessive stress hormone levels, such as aldesterone and cortisol levels The present invention provides a method of increasing or maintaining 11-deoxycortisol levels levels in a subject by administering a therapeutically efficient dose of a compound of formula (I).

The present invention provides a method of increasing or maintaining adreonocorticotropin levels levels in a subject by administering a therapeutically efficient dose of a compound of formula (I).

The present invention provides a method of increasing or maintaining 11-deoxycorticosterone levels in a subject by administering a therapeutically efficient dose of a compound of formula (I).

The present invention provides a method of increasing or maintaining adrenal androgens levels levels in a subject by administering a therapeutically efficient dose of a compound of formula (I).

The present invention provides the use of a compound of Formula (I) as pleiotropic modifier of adrenal steroidogenesis in a subject.

It further provides the use of a compound according to Formula (I) for the preparation of a pharmaceutical composition for the treatment of a disorder, disease or condition characterised by excessive stress hormone levels and/or insufficient androgen hormone levels.

It further provides a pharmaceutical composition comprising a compound according to formula (I) for use in the treatment of a disorder, disease or condition characterised by excessive stress hormone levels and/or insufficient androgen hormone levels. Such diseases or disorders can be heart failure, cachexia, acute coronary syndrome, chronic stress syndrome, hypercortisolemia, cushing's syndrome or metabolic syndrome.

It further provides the use of a compound of the present invention for the preparation of a pharmaceutical composition for the treatment of a disorder or disease or condition characterised by excessive stress hormone levels and or insufficient androgen hormone levels such as such as heart failure, cachexia, acute coronary syndrome, chronic stress syndrome, cushing's syndrome or metabolic syndrome.

In another aspect, the present invention provides methods of treating diseases or disorders characterised by excessive stress hormone levels and or insufficient androgen hormone levels by administering to a subject a therapeutically effective amount of a pharmaceutical composition comprising a compound according to Formula (I) and a pharmaceutically acceptable carrier. In another aspect, such diseases or disorders can be heart failure, cachexia, acute coronary syndrome, chronic stress syndrome, cushing's syndrome or metabolic syndrome.

In one embodiment, the present invention provides methods of administering to a subject a therapeutically effective amount of a pharmaceutical composition comprising a compound according to Formula (I) and a pharmaceutically acceptable carrier, to treat diseases or disorders characterised by excessive stress hormone levels and or insufficient androgen hormone levels. In another aspect, such diseases or disorders can be heart failure, cachexia, acute coronary syndrome, chronic stress syndrome, hypercortisolemia, cushing's syndrome or metabolic syndrome; in particular heart failure, cachexia, acute coronary syndrome, chronic stress syndrome, cushing's syndrome or metabolic syndrome.

Whenever used above, heart failure could be both acute heart failure and chronic heart failure. Acute heart failure could be acute decompensated heart failure. Chronic heart failure could be associated with impaired exercise tolerance and or with muscle weakness. Cachexia could be cardiac cachexia, COPD-induced cachexia, cirrhosis-induced cachexia tumor-induced cachexia or viral (HIV)-induced cachexia. Chronic stress syndrome may include depression, hyperglycemia and immunesuppression. Cushing's syndrome can include hypercortisolism due to adrenocortical, pituitary or ectopic tumors. Metabolic syndrome could include obesity, diabetes, hypertension, dyslipidemia and atherosclerosis. The compounds of Formula (I) have adrenal hormone-modifying properties in diseases or conditions characterised by increased stress hormone levels and/or decreased androgen hormone levels as shown in the experimental section.

A pharmaceutical composition comprising a compound of the present invention may be prepared according to methods known in the art. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

The pharmaceutical composition according to the present invention can be in unit dosage of at least 0.05 or 1 mg or greater of the compounds described herein as the active ingredient, such as of from 0.01 mg to 1000 mg, of from 0.01 mg to 500 mg, of from 0.01 to 50 mg, of from 0.01 mg to 5 mg, of from 0.01 to 2 mg or of from 0.1 mg to 2 mg of active ingredient; such as in unit dosage of at least 0.05 or 1 mg or of from 4 mg to 100 mg, for example of from 2 mg to 50 mg, of the compounds described herein as the active ingredient for a subject of about 50-70 kg. For example, the unit dosage can contain 1-1000 mg of active ingredient for a subject of about 50-70 kg, about 1-500 mg, about 1-50 mg, about 0.5-5 mg, 0.1-1 mg or about 0.05-0.5 mg of active ingredient. The dosage regimen utilizing the compounds described herein can be selected in accordance with a variety of factors including type, species, age, weight, sex, the type of disease or disorder to be treated, the severity of the disease or disorder to be treated, the route of administration, and the particular compound or salt employed. A physician, clinician or veterinarian of ordinary skill can readily determine the effective amount of each of the active ingredients necessary to prevent, treat or inhibit the progress of the disorder or disease.

The above-cited dosage properties are demonstrable in vitro (See PCT applications PCT/US2007/018660 & WO2007/065942A2) and in vivo tests (See Example 1 below) using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between 0.001-15 mg/kg, preferably between 0.003-0.05 mg/kg.

Listed below are definitions of various terms used throughout the specification:

The term "stress hormone", as used herein, relates to a hormone which is secreted in response to an unusual exposure to life. The stress response involves the activation of both the sympathetic adrenomedullary system with the secretion of epinephrine and norepinephrine, and the hypothalamic pituitary adrenocortical (HPA) system with the secretion of cortisol. Examples of stress hormones are, for example described in Table 1 in WO2007/105203, which is incorporated herein by reference. In a preferred embodiment, a stress hormone is aldosterone or cortisol, preferably cortisol.

The term "increased stress hormone levels" or "excessive stress hormone levels" is used herein to indicate that the level of hormone levels is statistically significantly raised relative to that of other parameters, such as aldosterone to plasma renin activity, or is statistically significantly raised relative to normal clinical reference values. For example, stress hormone levels are increased if the level of aldosterone is above 277 μM at rest or if the level of cortisol is above 552 nM in the morning, as described, for example in Endocrinology $9^{th}$ eidtions (Editors J. D. Wilson, D. W. Foster, H. M. Kronenberg, P. R. Larsen) W. B. Saunders Co., Philadelphia, 1988.

The term "reducing or inhibiting the activities of excessive stress hormone levels", as used herein, means any improvement in preventing, controlling, delaying, abating or mitigating relative and/or absolute increased or excessive stress hormone dysbalances leading to pathophysiology. Although the term "inhibiting" is not intended to be restricted to the normalization of stress hormone levels, it also includes the possibility that stress hormone levels are entirely normalized to clinical reference values.

The term "reducing or inhibiting the synthesis excessively produced stress hormone levels", as used herein, means any improvement in preventing, controlling, delaying, abating or mitigating relative and/or absolute increased or excessive stress hormone dysbalances leading to pathophysiology. Although the term "inhibiting" is not intended to be restricted to the normalization of stress hormone levels, it also includes the possibility that stress hormone levels are entirely normalized to clinical reference values.

The term "androgen hormone", as used herein, relates to male sex hormones and includes, for example, dehydroepiandrosterone sulphate (DHEAS), dehydroepiandrosterone (DHEA), androstenedione (A), testosterone (T) and dihydrotestosterone (DHT).

The terms "decreased androgen hormone levels" or "insufficient androgen hormone levels" are used herein to indicate that the level of androgen levels is statistically significantly lowered relative to that of other parameters, or is statistically significantly lowered relative to normal clinical reference values. For example, androgen hormone levels are decreased or insufficient if the level of androstendione is, for example, below 2619 μM or if the level of dehydroandrosterone is, for example, below 6.94 nM, as described, for example in Endocrinology $9^{th}$ editions (Editors J. D. Wilson, D. W. Foster, H. M. Kronenberg, P. R. Larsen) W. B. Saunders Co., Philadelphia, 1988.

The term "reducing or inhibiting the activity of steroidogenic enzymes that indirectly lead to insufficient androgen hormone levels", as used herein, means any improvement in preventing, controlling, delaying, abating or mitigating relative and/or absolute decreased or insufficient androgen hormone dysbalances leading to pathophysiology. Although the term "inhibiting" is not intended to be restricted to the normalization of androgen hormone levels, it also includes the possibility that androgen hormone levels are entirely normalized to clinical reference values.

The term "maintain" or "maintaining", when referring to hormone levels is used herein to mean an improvement in preventing, controlling or delaying relative and/or absolute decreased/insufficient androgen hormone levels and/or relative and/or absolute increased/excessive stress hormone levels.

The term "lower" or "lowering", when referring to stress hormone levels is used herein to mean any improvement in abating relative and/or absolute increased/excessive stress hormone levels.

The term "increase" or "increasing", when referring to androgen hormone levels is used herein to mean any improvement in mitigating relative and/or absolute decreased/insufficient androgen hormone levels.

As used herein, the term "abnormal" refers to an activity or feature which differs from a normal activity or feature.

The term "abnormal activity", as used herein, refers to any derangement of normal function. The abnormal activity can be stronger or weaker than the normal activity. In one embodiment, the "abnormal activity" refers to either over- or under-activity of, for example, and hormone, as defined herein.

The term "activity", as used herein, refers to any specific activity that a molecule is capable of performing or encoding. For example activity may be that a molecule is capable of associating with a specific binding partner with a specific affinity, capable of catalyzing a specific reaction, capable of inhibiting a specific reaction or capable of effecting a particular cellular response.

The term "expression", as used herein, is to be understood as defined, for example in Maniatis et al "Molecular Cloning: A Laboratory Manual" Cold Spring Harbor Laboratory Press: $2^{nd}$ Edition, 1989, for example, it refers to the accumulation of a molecule, such as an hormone as defined herein.

The term "pleiotropic adrenal hormone-modifying agent", as used herein, is to be understood as a molecule, such as a compound of formula (I) as defined herein, which inhibits the synthesis of both, aldosterone and cortisol, while it increases the levels of ACTH, 11-deoxycorticosterone and the synthesis of the adrenal androgens, androstendione and dehydroepiandrosterone.

The term "substituted", as used herein, refers to one or more substituents, for example one or two substituents, for example substituents as defined herein for a compound of formula (I).

The term "Cushing's syndrome" is also referred to as hyperadrenocorticism or hypercorticism. Cushing's syndrome can include hypercortisolism due to adrenocortical, pituitary or ectopic tumors.

For the purpose of this invention, the compound of formula (I), as defined herein, refers to both the free form as well as any pharmaceutical acceptable salt thereof.

EXPERIMENTAL SECTION

The following examples illustrate the above-described invention. However, it is not intended to restrict the scope of this invention in any manner. Other embodiments will be evident to a person skilled in the art whilst reading the foregoing detailed description The scope of the present invention are not limited to the above examples, but are encompassed by the following claims.

Example 1

In Vitro Rat CYP11B1 Assay

Complete EDTA-free protease inhibitor tablets were obtained from Roche Applied Science (Indianapolis, Ind.). Dulbecco's modified Eagle medium (DMEM), antibiotic, geneticin, hygromycin, and fetal bovine serum (FBS) were products of Invitrogen (Carlsbad, Calif.). NADPH Regeneration Solution A and Solution B were purchased from BD Biosciences Clontech (Palo Alto, Calif.). Anti-sheep PVT SPA beads and [1,2,6,7-$^3$H(N)]corticosterone were acquired from Amersham (Piscataway, N.J.) and PerkinElmer (Boston, Mass.), respectively.

Cell line V79-4 CYP11B1-adrenodoxin-adrenodoxin reductase #259 was maintained in DMEM supplemented with 10% FBS, 0.5× antibiotic, 800 μg/ml geneticin, and 250 μg/ml hygromycin (double-selection medium). For enzyme preparation, #259 cells were seeded in 150 mm dishes in double-selection medium. Following 2 days of growth, cells were washed once with PBS, scraped and collected in PBS, and centrifuged at 1,300 rpm for 6 min. Each pellet (representing 10 dishes of cells) was resuspended in 3 ml of ice-cold homogenization buffer (8.5 mM $MgCl_2$, 3.13 mM KCl, 7.59 mM NaCl, 50 mM Tris/HCl, pH 7.4, and one complete EDTA-free protease inhibitor tablet per 100 ml buffer), sonicated using a Branson Sonifier 450 with 6 pulses, and then placed on ice for 5 min. The sonication procedure was repeated 3 more times, with a 5 min rest on ice between sonications. The sonicated material was then spun at 500×g for 4 min to remove unbroken cells. The supernatant was brought to a final glycerol concentration of 5%, flash-frozen in liquid nitrogen, and stored at −80° C.

Material from frozen CYP11B1 preparations was thawed on ice on the day of experiment and then diluted in an ice-cold assay buffer containing 8.5 mM $MgCl_2$, 3.13 mM KCl, 7.59 mM NaCl, and 50 mM Tris/HCl, pH 7.4, to a protein concentration of 0.5-6 mg/ml. The CYP11B1 assays were performed in 96-well U-bottom non-tissue-culture-treated plates. Depending on the experiment, 50 to 300 μg of protein in 35 μl was incubated with 75 μl of assay buffer or a compound at the desired concentration and 20 μl of substrate mix (1.08× NADPH Regeneration Solution A, 6.5×NADPH Regeneration Solution B, 811 μM NADPH, and 3.25 μM 11-deoxycorticosterone in assay buffer) for up to 4 hr at 25° C. in a shaking incubator. The reaction was stopped by adding 10 μl of 1.4% Triton X-100 and briefly shaking the plates. Plates were then centrifuged at 2,400 rpm for 6 min, and 50 μl of supernatant was removed for measurement of corticosterone content by scintillation proximity assay (SPA).

Measurement of corticosterone was performed using a 96-well plate format. Each test sample (50 μl) was incubated with 0.02 μCi of [1,2,6,7-$^3$H(N)]corticosterone and 0.3 μg of anti-corticosterone antibody in PBS containing 0.1% Triton X-100, 0.1% bovine serum albumin, and 12% glycerol in a total volume of 200 μl at room temperature for 1 hr. Anti-sheep PVT SPA beads (50 μl) were then added to each well and incubated overnight at room temperature prior to counting in a Microbeta plate counter. The amount of corticosterone in each sample was calculated by comparing with a standard curve generated using known quantities of the hormone.

Full concentration-response curves of an inhibitor were performed at least 3 times. The $IC_{50}$ values were derived using a non-linear least squares curve-fitting program from IDBS XLfit. It has been found that the compounds within the scope of the present invention, particularly the specific compounds disclosed herein are active CYP11B1 inhibitors having $IC_{50}$ ranging from 0.3 nM to 600 nM.

Example 2

In Vitro Rat CYP11B2 Assay

Cell line V79-4 rCYP11B2-adrenodoxin-adrenodoxin reductase #305 is maintained in DMEM supplemented with 10% FBS, 0.5× antibiotic, 800 µg/ml geneticin, and 250 µg/ml hygromycin (double-selection medium). For enzyme preparation, #305 cells are seeded in 150 mm dishes (double selection medium) with an approximate surface area split of 1:15 from T-185 flask cultures growing at 75-85% confluence. Following 2 days of growth, cells are washed once with PBS, scraped and collected in PBS, and centrifuged at 1,300 rpm for 6 min. Each pellet (representing 10 dishes of cells) is resuspended in 3 ml of ice-cold homogenization buffer (8.5 mM MgCl2, 3.13 mM KCl, 7.59 mM NaCl, 50 mM Tris/HCl, pH 7.4, and one complete EDTA-free protease inhibitor tablet per 100 ml buffer), sonicated using a Branson Sonifier 450 with 6 pulses, and then placed on ice for 5 min. The sonication procedure is repeated 3 more times, with a 5 min incubation on ice between sonications. The sonicated material is then spun at 500×g for 4 min to remove unbroken cells. The supernatant is brought to a final glycerol concentration of 5%, flash-frozen in liquid nitrogen, and stored at −80° C.

Material from frozen CYP11B2 preparations is thawed on ice on the day of experiment and then diluted in an ice-cold assay buffer containing 8.5 mM MgCl2, 3.13 mM KCl, 7.59 mM NaCl, and 50 mM Tris/HCl, pH 7.4, to a protein concentration of 0.25-1.5 mg/ml. The CYP11B2 assay is performed in 96-well U-bottom non-tissue-culture-treated plates. Depending on the experiment, 14 to 84 µg of protein in 55 µl is incubated with 75 µl of assay buffer or a compound at the desired concentration and 20 µl of substrate mix (1.25× NADPH Regeneration Solution A, 7.5×NADPH Regeneration Solution B, 935.75 µM NADPH, and 15 µM 11-deoxycorticosterone in assay buffer) for up to 5 hr at 25° C. in a shaking incubator. The reaction is stopped by adding 10 µl of 1.6% Triton X-100 and briefly shaking the plates. Plates are then centrifuged at 2,400 rpm for 6 min, and 100 µl of supernatant is removed for measurement of aldosterone content by scintillation proximity assay (SPA).

Measurement of aldosterone is performed using a 96-well plate format. Each test sample (2-10 µl of cell culture medium or 100 µl of cell homogenate) is incubated with 0.02 µCi of [1,2,6,7-3H(N)]aldosterone and 0.3 µg of anti-aldosterone antibody in PBS containing 0.1% Triton X-100, 0.1% bovine serum albumin, and 12% glycerol in a total volume of 200 µl at room temperature for 1 hr. Anti-mouse PVT SPA beads (50 µl) are then added to each well and incubated for 4 hr at room temperature prior to counting in a Microbeta plate counter. The amount of aldosterone in each sample is calculated by comparing with a standard curve generated using known quantities of the hormone.

Full concentration-response curves of an inhibitor are performed at least 3 times. The IC50 values are derived using a non-linear least squares curve-fitting program from DBS XLfit.

Example 3

In Vitro Human CYP11B1 Assay

Complete EDTA-free protease inhibitor tablets were obtained from Roche Applied Science (Indianapolis, Ind.). Dulbecco's modified Eagle medium (DMEM), antibiotic, geneticin, hygromycin, and fetal bovine serum (FBS) were products of Invitrogen (Carlsbad, Calif.). NADPH Regeneration Solution A and Solution B were purchased from BD Biosciences Clontech (Palo Alto, Calif.). Anti-mouse PVT SPA beads and [1,2,6,7-$^3$H(N)]hydrocortisone were acquired from Amersham (Piscataway, N.J.) and PerkinElmer (Boston, Mass.), respectively.

Cell line V79-4 CYP11B1-adrenodoxin-adrenodoxin reductase #618 was maintained in DMEM supplemented with 10% FBS, 0.5× antibiotic, 800 µg/ml geneticin, and 250 µg/ml hygromycin (double-selection medium). For enzyme preparation, #618 cells were seeded in 150 mm dishes at $6.75 \times 10^5$ cells per dish in double-selection medium. Following 4 days of growth, cells were washed once with PBS, scraped and collected in PBS, and centrifuged at 1,300 rpm for 6 min. Each pellet (representing 10 dishes of cells) was resuspended in 3 ml of ice-cold homogenization buffer (8.5 mM MgCl$_2$, 3.13 mM KCl, 7.59 mM NaCl, 50 mM Tris/HCl, pH 7.4, and one complete EDTA-free protease inhibitor tablet per 100 ml buffer), sonicated using a Branson Sonifier 450 with 6 pulses, and then placed on ice for 5 min. The sonication procedure was repeated 3 more times, with a 5 min rest on ice between sonications. The sonicated material was then spun at 500×g for 4 min to remove unbroken cells. The supernatant was brought to a final glycerol concentration of 5%, flash-frozen in liquid nitrogen, and stored at −80° C.

Material from frozen CYP11B1 preparations was thawed on ice on the day of experiment and then diluted in an ice-cold assay buffer containing 8.5 mM MgCl$_2$, 3.13 mM KCl, 7.59 mM NaCl, and 50 mM Tris/HCl, pH 7.4, to a protein concentration of 0.5-6 mg/ml. The CYP11B1 assays were performed in 96-well U-bottom non-tissue-culture-treated plates. Depending on the experiment, 50 to 300 µg of protein in 35 µl was incubated with 75 µl of assay buffer or a compound at the desired concentration and 20 µl of substrate mix (1.08× NADPH Regeneration Solution A, 6.5×NADPH Regeneration Solution B, 811 µM NADPH, and 3.25 µM 11-deoxycortisol in assay buffer) for up to 4 hr at 25° C. in a shaking incubator. The reaction was stopped by adding 10 µl of 1.4% Triton X-100 and briefly shaking the plates. Plates were then centrifuged at 2,400 rpm for 6 min, and 50 µl of supernatant was removed for measurement of cortisol content by scintillation proximity assay (SPA). Measurement of cortisol was performed using a 96-well plate format. Each test sample (50 µl) was incubated with 0.02 µCi of [1,2,6,7-$^3$H(N)]hydrocortisone and 0.3 µg of anti-cortisol antibody in PBS containing 0.1% Triton X-100, 0.1% bovine serum albumin, and 12% glycerol in a total volume of 200 µl at room temperature for 1 hr. Anti-mouse PVT SPA beads (50 µl) were then added to each well and incubated overnight at room temperature prior to counting in a Microbeta plate counter. The amount of cortisol in each sample was calculated by comparing with a standard curve generated using known quantities of the hormone. Full concentration-response curves of an inhibitor were performed at least 3 times. The IC$_{50}$ values were derived using a non-linear least squares curve-fitting program from IDBS XLfit. It has been found that the compounds within the scope of the present invention, particularly the specific compounds disclosed herein are active CYP11B1 inhibitors having IC$_{50}$ ranging from 0.2 nM to 200 nM.

Example 4

In Vitro Human CYP11B2 (aldesterone) Assay

Human adrenocortical carcinoma NCI-H295R cell line was obtained from American Type Culture Collection (Manassas, Va.). Insulin/transferrin/selenium (ITS) —A supplement (100×), DMEM/F-12, antibiotic/antimycotic (100×), and fetal bovine serum (FBS) were purchased from Invitrogen (Carlsbad, Calif.). Anti-mouse PVT scintillation proximity assay (SPA) beads and NBS 96-well plates were obtained from GE Health Sciences (Piscataway, N.J.) and Corning (Acton, Mass.), respectively. Solid black 96-well flat bottom plates were purchased from Costar (Corning, N.Y.). Aldosterone and angiotensin (Ang II) were purchased from Sigma (St. Louis, Mo.). D-[1,2,6,7-$^3$H(N)]aldosterone was acquired from PerkinElmer (Boston, Mass.). Nu-serum was a product of BD Biosciences (Franklin Lakes, N.J.).

For in vitro measurement of aldosterone activity, human adrenocortical carcinoma NCl-H295R cells are seeded in NBS 96-well plates at a density of 25,000 cells/well in 100 μl of a growth medium containing DMEM/F12 supplemented with 10% FCS, 2.5% Nu-serum, 1 μg ITS/ml, and 1× antibiotic/antimycotic. The medium is changed after culturing for 3 days at 37° C. under an atmosphere of 5% $CO_2$/95% air. On the following day, cells are rinsed with 100 μl of phosphate-buffered saline (PBS) and incubated with 100 μl of treatment medium containing 1 μM Ang II and a compound at different concentrations in quadruplicate wells at 37° C. for 24 hr. At the end of incubation, 50 μl of medium is withdrawn from each well for measurement of aldosterone production by an SPA using mouse anti-aldosterone monoclonal antibodies.

Measurement of aldosterone activity can also be performed using a 96-well plate format. Each test sample is incubated with 0.02 μCi of D-[1,2,6,7-$^3$H(N)]aldosterone and 0.3 μg of anti-aldosterone antibody in PBS containing 0.1% Triton X-100, 0.1% bovine serum albumin, and 12% glycerol in a total volume of 200 μl at room temperature for 1 hr. Anti-mouse PVT SPA beads (50 μl) are then added to each well and incubated overnight at room temperature prior to counting in a Microbeta plate counter. The amount of aldosterone in each sample is calculated by comparing with a standard curve generated using known quantities of the hormone.

Example 5

Determination of $IC_{50}$ Values for CYP11B1 and CYP11B2

The excretion of aldosterone, cortisol, corticosterone and estradiol/estrone into the culture medium can be detected and quantified by commercially available, specific monoclonal antibodies in radioimmunoassays in accordance with the manufacturer's instructions. Inhibition of the release of certain steroids can be used as a measure of the respective enzyme inhibition by the added test compounds. The dose-dependent inhibition of enzymic activity by a compound is calculated by means of an inhibition plot which is characterized by an IC50. The IC50 values for active test compounds are ascertained by a simple linear regression analysis in order to construct inhibition plots without data weighting. The inhibition plot is calculated by fitting a 4-parameter logistic function to the raw data points using the least squares method. The equation of the 4-parameter logistic function is calculated as follows: $Y=(d-a)/((1+(x/c)b))+a$, where: a=minimum data level, b=gradient, I c=ICED, d=maximum data level, x=inhibitor concentration.

The inhibition activity of aldosterone production can also be expressed in percentage inhibition (% inhibition) at a given concentration (e.g. % inhibition at 1 μM), which is the aldosterone level when the cell is treated with the given concentration of a compound of this invention (e.g. concentration of 1 μM) versus the aldosterone excretion when cell is free of the compound of the invention:

% inhibition aldosterone production=$[(Y-X)/Y]\times 100$ wherein X is the level of aldosterone when the cell is treated with a compound according to anyone of Formulae I to IVB; or pharmaceutically acceptable salt thereof, and Y is the level of aldosterone when the cell is free of compound according to anyone of Formulae I to IVB, or pharmaceutically acceptable salt thereof.

The inhibition activity of CYP11B1 production can also be expressed in percentage inhibition (% inhibition) at a given concentration (e.g. % inhibition at 1 μM), which is the cortisol level when cell is treated with the given concentration of a compound of the invention (e.g. concentration of 1 μM) versus the cortisol excretion when cell is free of the compound of the invention.

% inhibition cortisol production=$[(Y'-X')/Y']\times 100$ wherein X' is the level of cortisol when the cell is treated with a compound of Formulae I to IVB; and Y' is the level of cortisol when the cell is free of compound of Formulae I to IVB. Using the test assays for measuring CYP11B1 (cortisol) and CYP11B2 (aldosterone), as described above, compounds of the invention exhibited inhibitory efficacy as shown in Table 1.

TABLE 1

Data from Example 1, 2, 3 and 4

| Compound | Human CYP11B1 nM | Human CYP11B2 nM | Rat CYP11B1 nM | Rat CYP11B2 nM |
|---|---|---|---|---|
| 4'-fluoro-6-(6,7,8,9-tetrahydro-5H-imidazo[1,5-a]azepin-5-yl)biphenyl-3-carbonitrile enantiomer A** (Example 25 as described in WO2007/024945) | 0.3 | 0.4 | 0.3 | 1.0 |
| 3-bromo-4-(6,7,8,9-tetrahydro-5H-imidazo[1,5-a]azepin-5-yl)benzonitrile racemate** (Example 23 as described in WO2007/024945) | 0.2 | 1.2 | 1.0 | 1.0 |
| 5-(2-chloro-4-cyanophenyl)-N-(4-methoxybenzyl)-N-methyl-6,7-dihydro-5H-pyrrolo[1,2-c]imidazole-5-carboxamide enantiomer B** (Example 9-9 as described in WO2007/024945) | 0.8 | 2.7 | 2.0 | 5.0 |
| 4-(6,7-Dihydro-5H-pyrrolo[1,2-c]imidazol-5-yl)-3-fluorobenzonitrile enantiomer B** ((R) enantiomer, as described in Exampe 3, in WO2007/024945) | 1.8 | 0.7 | 495 | 110 |

**Please refer to WO2007/024945 for details.

Example 6

In Vivo CYP11B1 Assay

The in vivo effects of compounds on plasma aldosterone concentration (PAC) and plasma glucocorticoid (corticosterone) concentration (PCC) were evaluated in conscious rats.

Male Sprague-Dawley rats (~400-600 g body weight) were surgically instrumented with a femoral arterial and venous catheter. The catheters were exteriorized from the lower back through a stainless steel spring and swivel system that enabled the rats to move freely at all times. Rats were allowed at least one week to recover from the surgery before initiating the experiments.

On the morning of the experiment, a pretreatment blood sample was collected on heparin from the arterial catheter. The blood samples were spun in a refrigerated centrifuge to generate plasma. The plasma was stored frozen at −70° C. until the later measurement of PAC and PCC (by radioimmunoassay). Adrenocorticotropic hormone (ACTH(1-24), referred to herein as ACTH) was then administered as an intravenous (i.v.) bolus (100 ng/kg) followed by a continuous i.v. infusion (30 ng/kg/min) for 9 hours. After one hour of infusion, a baseline (time 0) blood sample was withdrawn from the arterial catheter and processed and stored as described above. The rats were then dosed (typically 0.01 to 100 mg/kg) with the test compound p.o. by oral gavage or parenterally via the arterial catheter (i.a.). Compounds were formulated in an appropriate vehicle (e.g., water (p.o.) or saline (i.a.)) at a physiologically compatible volume (typically 1-2 ml/kg). Additional blood samples were withdrawn at 0.083 (i.a. only), 0.25, 0.5, 1, 2, 3, 4, 5, 6, 7, 8, and 24 hours after dosing with compound and processed and stored as above for later determination of PAC, PCC, and plasma compound concentration (by LC/MS/MS). Oral bioavailability and traditional pharmacokinetic (PK) parameters were estimated from the plasma compound concentrations.

In the control rats, ACTH administration resulted in a sustained increase in PAC by ~10-fold (from ~0.26 nM to ~2.5 nM) and PCC by ~4- to 5-fold (from ~300 nM to ~1340 nM) for the duration of the 9-hour experiment. In contrast, administration of a test compound time- and dose-dependently lowered PAC and PCC by 0 to 97% depending on the compound's inherent CYP11B2 and CYP11B1 inhibitory potencies and its ADME (absorption, distribution, metabolism, excretion) properties. Based on the plasma compound concentration at each dose, the PK/PD (pharmacodynamic) profiles (reduction of PAC and PCC) of each compound were determined. Table 2 below summarizes the CYP11B1 and CYP11B2 inhibitory activities of representative compounds.

TABLE 2

| Compound | Dose (mg/kg) | | % Reduction from baseline | |
|---|---|---|---|---|
| | | | t = 1 h | 8 h |
| 4'-fluoro-6-(6,7,8,9-tetrahydro-5H-imidazo[1,5-a]azepin-5-yl)biphenyl-3-carbonitrile enantiomer A** (Example 25 as described in WO2007/024945) | 3 (i.a.) | PCC PAC | 89 83 | 43 76 |
| 3-bromo-4-(6,7,8,9-tetrahydro-5H-imidazo[1,5-a]azepin-5-yl)benzonitrile racemate** (Example 23 as described in WO2007/024945) | 10 (p.o.) | PCC PAC | 70 79 | 87 89 |
| 5-(2-chloro-4-cyanophenyl)-N-(4-methoxybenzyl)-N-methyl-6,7-dihydro-5H-pyrrolo[1,2-c]imidazole-5-carboxamide enantiomer B** (Example 9-9 as described in WO2007/024945) | 30 (i.a.) | PCC PAC | 76 23 | 78 59 |
| 4-(6,7-Dihydro-5H-pyrrolo[1,2-c]imidazol-5-yl)-3-fluorobenzonitrile enantiomer B** ((R) enantiomer, as described in Exampe 3, in WO2007/024945) | 10 (p.o.) | PCC PAC | 24 65 | 30 72 |

**Please refer to WO2007/024945 for details.

Example 7

A pilot, single-blind, forced-titration study was performed to assess the hormonal effects of a compound of formula (I), 4-[(5R)-6,7-dihydro-5H-pyrrolo[1,2-c]imidazol-5-yl]-3-fluororbenzonitrile dihydrogen phosphate, in patients with diagnosed primary hyperaldosteronism. The clinical study was designed, implemented and reported in accordance with the ICH harmonized tripartite guidelines for good clinical practice with applicable local regulations. Each patient participated in a screening/washout period, a 2-week placebo run-in period, a 4-week treatment period, and a 1-week placebo wash-out. The treatment period consisted of the oral administration of compound of formula (I) twice daily at a dose of 0.5 mg for two weeks followed by a dose increase to 1.0 mg twice daily for another 2 weeks. Blood samples were taken at baseline, day 1 and 2, day 8, day 15, day 22, day 29 and 30 (all at predose i.e., 12 h after the last dose), and at the final study day 36. Each sample was assessed for aldosterone and immunoreactive active renin, 11-deoxycorticosterone, cortisol, 11-deoxycortisol and adrenocorticotropin (ACTH) after subjects were at rest for at least 60 minutes to avoid any postural or stress-induced value changes. Plasma aldosterone was measured using a commercially available radioimmunoassay kit (DPC, France). Plasma Active Renin was measured using the two monoclonal antibodies 3E8 and 125I-4G1 in a commercially available immunoradiometric kit (CisBio, France). Plasma 11-deoxycorticosterone, cortisol and 11-deoxycortisol were measured using a standardized LC-MS/MS method. Plasma ACTH was measured using a commercially available immunoradiometric kit (CisBio, France).

Figure 2:
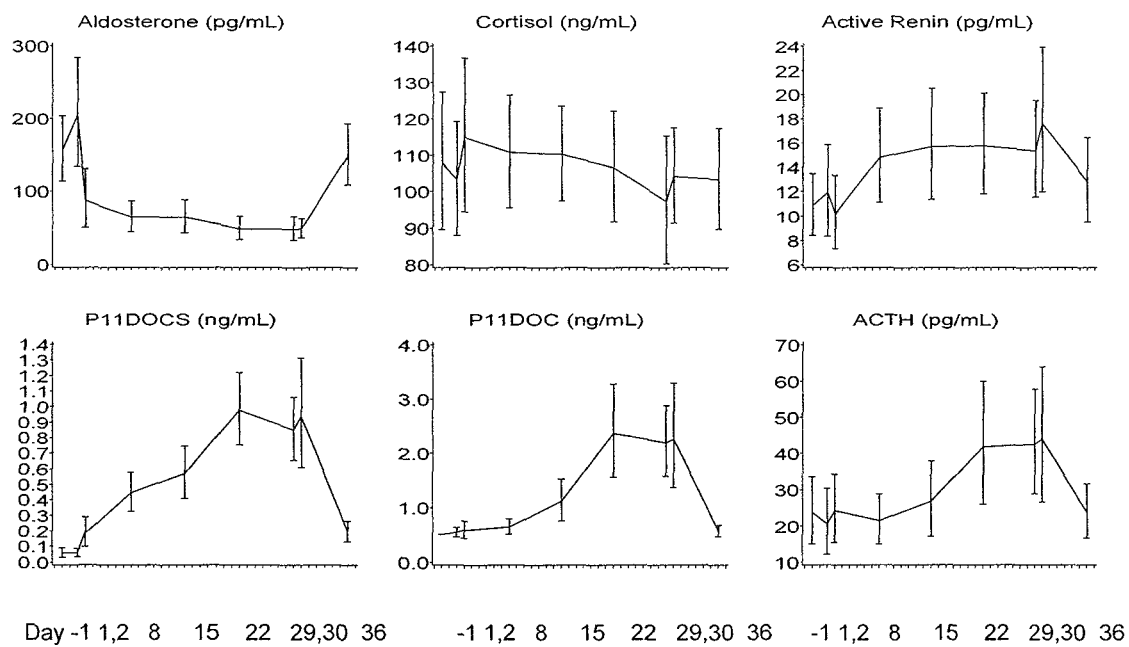
FIG. 2, the administration of a compound of formula (I), 4-[(5R)-6,7-dihydro-5H-pyrrolo[1,2-c]imidazol-5yl]-3-fluororbenzonitrile dihydrogen phosphate to patients with primary hyperaldosteronism over a 2-times 2-week period.

Statistical analysis of the pharmacodynamic biomarker were summarized using descriptive statistics as well as graphical and/or regression methods. The administration of a compound of formula (I), 4-[(5R)-6,7-dihydro-5H-pyrrolo[1,2-c]imidazol-5-yl]-3-fluororbenzonitrile dihydrogen phosphate to patients with primary hyperaldosteronism over a 2-times 2-week period is shown in FIG. 2 and elicited as anticipated potent aldosterone suppression that was reflected by an increased active renin level but also by an unexpectedly high build-up of the precursor steroid 11-deoxycorticosterone. The accumulation of 11-deoxycorticosterone (P11DOCS) was stimulated by increased ACTH levels. The increased adrenocorticotropin levels resulted from inhibition of cortisol synthesis via 11-beta-hydroxylase as reflected by decreasing cortisol levels and an accumulation of the enzyme substrate 11-deoxycortisol (P11DOC). The increased 11-deoxycorticosterone levels in presence of inhibited stress hormone synthesis are shifted towards increased synthesis of the adrenal androgens androstendione and dehydroepiandrosterone (see FIG. 1, a diagram for adrenal steroidogenesis). Thus, the compound of formula (I), exhibited the pharmacological profile of a pleiotropic adrenal hormone-modifying agent as it inhibits the synthesis of both, aldosterone and cortisol, while it increases the levels of ACTH, 11-deoxycorticosterone and finally the synthesis of the adrenal androgens, androstendione and dehydroepiandrosterone.

Example 8

An open-label, single arm, sequential dose-escalation, multi-center study in patients with Cushing's disease is performed as described herein below.

The study consists of a 10-14-day baseline period, a 10-week treatment period consisting of biweekly treatment with escalating doses and a 14-day washout period followed by a Study Completion evaluation at 14 days after the last drug administration. The study drug is applied at escalating doses of 2 mg, 5 mg, 10 mg, 20 mg and 50 mg twice daily (bid) each for a two week period (see study timeline below). The optimal therapeutic dose is dependent on the severity and responsiveness of the underlying pathological condition.

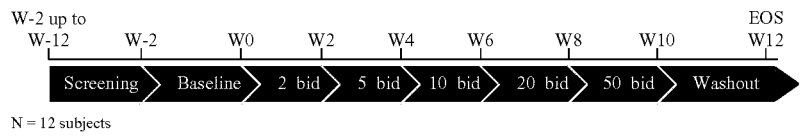

N = 12 subjects

Population: The study population is comprised of male and female patients with endogenous hypercortisolism due to increased ACTH [Adrenocorticotropic Hormone] production from the pituitary (Cushing's disease).

Male or female patients aged 18-75 years

Patients have confirmed Cushing's Disease as evidenced by:
  UFC [Urinary Free Cortisol]>1.5×ULN [Upper Limit of Normal] (Mean value of three 24-hour urine samples collected within 14 days)
  Morning plasma ACTH above 10 pg/mL Subjects are permitted to washout current drug therapy to meet these entry criteria if they have a known diagnosis of Cushing's disease.

Therapy: Subjects start on a dose of 2 mg b.i.d. of 4-[(5R)-6,7-dihydro-5H-pyrrolo[1,2-c]imidazol-5-yl]-3-fluorobenzonitrile dihydrogen phosphate and increase their dose every 2 weeks. The optimal therapeutic dose is determined by the treatment effect and tolerability of the intervention.

Efficacy/Pharmacodynamic Assessments: Efficacy assessments include urinary free cortisol, plasma ACTH, cortisol and renin, plasma and urine aldosterone, plasma and urine sodium and potassium, salivary cortisol and aldosterone and plasma insulin.

Safety Assessments: Safety assessments include physical examinations, ECGs (Electrocardiograms), vital signs, standard clinical laboratory evaluations (hematology, blood chemistry, urinalysis,) adverse event and serious adverse event monitoring.

Data Analysis: The primary efficacy variable is defined as the proportion of responders to 4-[(5R)-6,7-dihydro-5H-pyrrolo[1,2-c]imidazol-5-yl]-3-fluorobenzonitrile dihydrogen phosphate. A patient is considered to be a responder if the mean UFC level from the Week 10 24-hour urine samples is ≤1×ULN. Patients who discontinue for a disease or treatment related reason (e.g. death, adverse event, clinical disease progression etc.), or whose mean Week 10 24-hour UFC levels are higher than the normal limit are classified as non-responders. Patients who have only one baseline or post-baseline 24-hour UFC measurement will not be included in the primary efficacy analyses.

The invention claimed is:

1. A method of treating a disease or disorder characterized by increased stress hormone levels and/or decreased androgen hormone levels in a subject, comprising administering to the subject a therapeutically effective amount of a compound represented by formula (I):

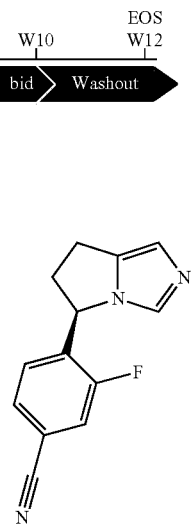

or a pharmaceutically acceptable salt thereof,
  wherein the disease or disorder is Cushing's syndrome, Cushing's disease or cachexia selected from cardiac cachexia, COPD-induced cachexia, cirrhosis-induced cachexia, tumor-induced cachexia, or viral (HIV)-induced cachexia, and
  wherein the treating a disease or disorder is partially or totally ameliorating the disease or disorder, partially or totally ameliorating at least one physical parameter of the disease or disorder, modulating the disease or disorder, or delaying the onset or development or progression of the disease or disorder.

2. The method according to claim 1 wherein said the compound of formula I is in the salt form of dihydrogen phosphate.

3. The method according to claim 1 wherein the disease or disorder is Cushing's syndrome.

4. The method according to claim 1 wherein the disease or disorder is Cushing's disease.

5. The method according to claim 1, wherein the disease or disorder is cachexia is selected from cardiac cachexia, COPD-induced cachexia, cirrhosis-induced cachexia, tumor-induced cachexia, or viral (HIV)-induced cachexia.

* * * * *